United States Patent [19]

Richards et al.

[11] Patent Number: 5,439,586

[45] Date of Patent: Aug. 8, 1995

[54] MAGNETIC FILTER WITH ORDERED WIRE ARRAY

[75] Inventors: Adrian J. Richards, Ashgrove, Australia; Peter M. Lansdorp, Vancouver, Canada

[73] Assignees: The Terry Fox Laboratory of the British Columbia Cancer Agnecy, Vancouver, Canada; The University of Southampton, Highfield, England

[21] Appl. No.: 121,098

[22] Filed: Sep. 15, 1993

[51] Int. Cl.$^6$ .............................................. B01D 35/06
[52] U.S. Cl. .................................... 210/222; 210/456
[58] Field of Search ............... 210/222, 223, 456, 695; 209/224, 232

[56] References Cited

U.S. PATENT DOCUMENTS

| | | | |
|---|---|---|---|
| 1,245,717 | 11/1917 | Henderson | 209/224 |
| 3,873,448 | 3/1975 | Isberg et al. | 210/222 |
| 4,452,773 | 5/1984 | Molday | 424/1.1 |
| 4,472,275 | 9/1984 | Yano | 210/222 |
| 4,544,482 | 10/1985 | Rupp | 210/222 |
| 4,698,302 | 6/1987 | Whitehead | 435/94 |
| 4,855,045 | 8/1989 | Reed | 210/223 |
| 4,868,109 | 9/1989 | Lansdorp | 435/28 |
| 4,910,148 | 3/1980 | Sorensen | 435/317.1 |

FOREIGN PATENT DOCUMENTS

| | | |
|---|---|---|
| 3720844 | 1/1989 | Germany . |
| 3827252 | 2/1990 | Germany . |
| 143814 | 8/1983 | Japan ................................ 210/222 |
| 153914 | 8/1985 | Japan ................................ 210/222 |
| 2122369 | 6/1984 | United Kingdom . |
| 90/04019 | 4/1990 | WIPO .. |

OTHER PUBLICATIONS

Areman et al., Bone Marrow Purging and Processing, pp. 379–385, 1990.
Rowley et al., Bone Marrow Purging and Processing, pp. 369–377, 1990.
Gerota et al., Cryobiology 19, p. 675, 1982.
Humblet et al., Marrow Transplantation, pp. 63–67, 1988.
Staerz et al., PNAS (USA), pp. 1453–1457, 1986.
Staerz et al., Immunol. Today, pp. 241–244, 1986.
Parker, Contemp. Physics, pp. 279–306, 1977.
Birss et al., Filtration and Separation, pp. 339–342, 1977.
Blevins, R. D., "Applied Fluid Dynamics Handbook", Van Nostrand Reinhold Co., New York, 1984.
Melville, D., et al., Nature 255:706, 1975.
Kato, K., and Radbruch, A., Cytometry 11:231, 1990.
Miltenyi, S., et al., Cytometry 11:231, 1990.
Molday, R. S., and Molday, L., FEBS. Lett. 170:232 1984.
Kemshead, J. T., Hematotherapy 1:35, 1992.
Kemshead, J. T., in Bone Marrow Processing and Purging, 293, Gee, A. P. Ed., C. R. C. Press, Inc., Boca Raton, Fla., 1991.
Gilmore, M. J. et al., Vox Sang., 45, 294, 1983.
Fara dji, A. et al., Vox Sang., 55, 133, 1988.
Beaujean, M. F. et al., Transfusion, 25, 152, 1985.
English, D. et al., Transfusion, 29, 12, 1989.
Jin, N., et al., Exp. Hematol. 15, 93, 1987.

(List continued on next page.)

*Primary Examiner*—Matthew O. Savage
*Attorney, Agent, or Firm*—Bereskin & Parr

[57] ABSTRACT

A device for separating magnetic materials from non-magnetic materials in a sample using an applied magnetic field includes an inverted upstream funnel containing a plurality of longitudinally spaced, non-magnetisable flow-smoothing surfaces extending transversely across the width of the funnel, a coaxial filter chamber coupled to the output end of the upstream funnel having mounted therein an ordered wire array of magnetisable wires and a coaxial downstream funnel containing a plurality of longitudinally spaced, non-magnetisable flow-smoothing surfaces extending transversely across the width of the downstream funnel. The device may be used to separate magnetically labelled materials from samples such as biological samples.

16 Claims, 2 Drawing Sheets

OTHER PUBLICATIONS

Molday, R. S., and MacKenzie, D., J. Immunol. Methods 52:353, 1982.

Staerz et al., Nature, 314:628, 1985.

Perez et al., Nature, 314:628, 1985.

Bach, J. F. in Leucocyte Typing, eds., Bernard A., Boumsell, L. Dausett, J., Milstein, C. and Schlossman, S. F.: Springer-Verlag. New York, 1984, pp. 661-664.

Thomas, T. E., et al., J. Immunol. Methods 120:221, 1989.

Watson, J. H. P., "High Gradient Magnetic Separation", Chapter 22 in: Solid-Liquid Separation, 3rd ed., Svarovsky, L. ed., Butterworths and Co. Publishers, 1990.

Wognum, A. W., et al., Cytometry 8:366, 1987.

Watson, J. H. P., "Theory of Capture of Particles in Magnetic High-Intensity Filters", IEEE Trans. Magn., vol. MAG-11, Nov. 5, 1975 pp. 1597-1599.

Gerber R. and Lawson, P., "The HGMS Filter Performance Exponential Law", IEEE Trans. Magn., vol. 25, Nov. 5, 1989.

MAGNETIC FILTER WITH ORDERED WIRE ARRAY

BACKGROUND OF THE INVENTION

The present invention relates to the application of high gradient magnetic separation (HGMS) to the process of separation and isolation of materials labeled magnetised particles.

A HGMS system consists of a filter of fine magnetisable wires placed in a strong magnetic field. This causes high gradient magnetic fields to be produced around the wires, allowing the capture of even very weakly magnetic particles upon the magnetised wires.

HGMS was first proposed during the search for the elusive magnetic monotone, and its first industrial application was the removal of staining iron from clay. Since then, numerous other industrial applications for HGMS have been developed, including mineral benefication, sewage and industrial effluent treatment, and nuclear fuel reprocessing. The first application of HGMS to the separation of human cells took place in 1975, when it was shown that erythrocytes (red blood cells) could be retained on a HGMS filter (Melville, D., et al., Nature 255:706, 1975). Because almost all human cells are relatively nonmagnetic in aqueous media, the desired cells must be specifically labeled with a magnetic material in order for HGMS to be used to its full potential. Typically, a magnetic material is attached to an antibody which identifies and allows the magnetic material to attach to the desired cell.

There are potentially a large number of applications of HGMS to the separation and isolation of biological cells. One example of this is in the treatment of leukaemia, whereby cancerous cells are separated and removed from the bone mirror of the patient, or alternatively, the pluripotent stem cells of the bone marrow (CD34 positive cells, known as the father cells of bone marrow) can be separated and purified.

There have been several attempts to apply HGMS to the separation and isolation of magnetically labelled CD34 positive cells, although the recoveries and purities achieved have been undesirably low (For example, see Kato, K., and Radbruch, A., Cytometry 14:384, 1993). Typically, attempts have employed an HGMS filter which consists of a random or semi-random array of stainless steel wire wool packed loosely into a column located in a strong magnetic field (Miltenyi, S. et al., Cytometry 11:231, 1990; Molday, R. S. and Molday, L., FEBS. Lett. 170:232, 1984; Kato, K and Radbruch, A., supra; Kemshead, J. T. in Hematotherapy 1:35, 1992; and Kemshead, J. T. in Bone Marrow Processing and Purging, 293, Gee, A.P. Ed., C.R.C. Press, Inc., Boca Raton, Fla., 1991).

Existing HGMS cell separation systems have difficulty in separating cell suspensions which exhibit the following characteristics: the desired cells have low and variable antigenic sites on their surfaces so they do not form a well defined labelled population, the desired cells are in variable and low abundance in the heterogenous cell population, highly adhesive cells which will adhere to any surface are present, and total cell numbers for separation are large (i.e. $>10^9$). Separation of CD34 positive cells from bone marrow is an extreme example of suspensions exhibiting these characteristics.

Therefore, there is a need for an improved cell separation system which addresses the problems associated with the prior art.

SUMMARY OF THE INVENTION

The present invention is directed to a filter device for separating magnetic materials from non-magnetic materials in a fluid using an applied magnetic field, which filter has a longitudinal axis along which fluid flows. The subject device comprises upstream flow expansion and distribution means, filter means, and downstream flow contraction and distribution means. The upstream flow expansion and distribution means uniformly distributes the flow as the container cross-section increases. It comprises an inverted funnel with a smaller input end and a larger output end, having a plurality of longitudinally spaced non-magnetisable flow smoothing surface means extending transversely of the axis across the funnel. The filter means is coupled to the output end of the upstream funnel and magnetically filters the magnetic material from the rest of the fluid when a magnetic field is applied thereto, while allowing non-magnetic material to pass through. This filter means comprises a coaxial filter chamber having mounted therein an ordered wire array of magnetisable wires. The downstream flow contraction and distribution means contracts and uniformly distributes the fluid which passes through the filter section. It comprises a funnel having a larger input end coupled to the filter chamber and a smaller output end, having a plurality of longitudinally spaced non-magnetisable flow smoothing surface means extending transversely of the axis across the funnel.

The filter device of the present invention preferably comprises conical funnels and a cylindrical filter chamber. The ordered wire array of the subject filter device preferably comprises a stack of cross-hatched magnetisable stainless steel wire meshes. The smoothing surfaces are preferably meshes made of weaved, non-magnetic stainless steel wires preferably spaced a minimum of 200 $\mu$m apart. The conical funnels preferably have smooth, polished and continuous inside surfaces, and the intersections between the cylindrical filter section and the conical funnel sections are preferably slightly chamfered, on the lower edge of the intersection.

The subject device may also comprise reinforcing means for reinforcing the ordered wire array against distortion due to fluid flow and the applied magnetic field, comprising crosslinking means for crosslinking ordered magnetisable wires and mesh support means for supporting arrays of ordered magnetisable wires. The crosslinking means may comprise an encapsulating coating such as silicone or teflon, applied to the wires at their junction. The mesh support means may comprise a plurality of longitudinally spaced pairs of transversely extending support wires.

The present invention also broadly contemplates a method of using the filter device of the invention in the separation of preselected materials from a sample. Preferably, a subpopulation of preselected cells or proteins are separated from a biological sample. One embodiment of the method of using the filter device of the invention to separate preselected materials from a sample comprises magnetically labelling the preselected materials in the sample; passing a sample containing the magnetically labelled materials through the filter device of the invention in the presence of a magnetic field; and isolating magnetically labelled materials. In a preferred embodiment the materials are magnetically labelled by providing a fluid containing magnetic or highly magnetisable particles; forming a complex of the magnetic or highly magnetisable particles and a substance capable of binding to the materials; reacting a sample containing the materials with the complexes so that the materials in the sample bind to the complexes to produce magnetically labelled materials.

BRIEF DESCRIPTION OF THE DRAWINGS

The invention will now be described with reference to the accompanying drawings, in which.

DETAILED DESCRIPTION OF THE DRAWINGS

Figures 1, 2, 3:
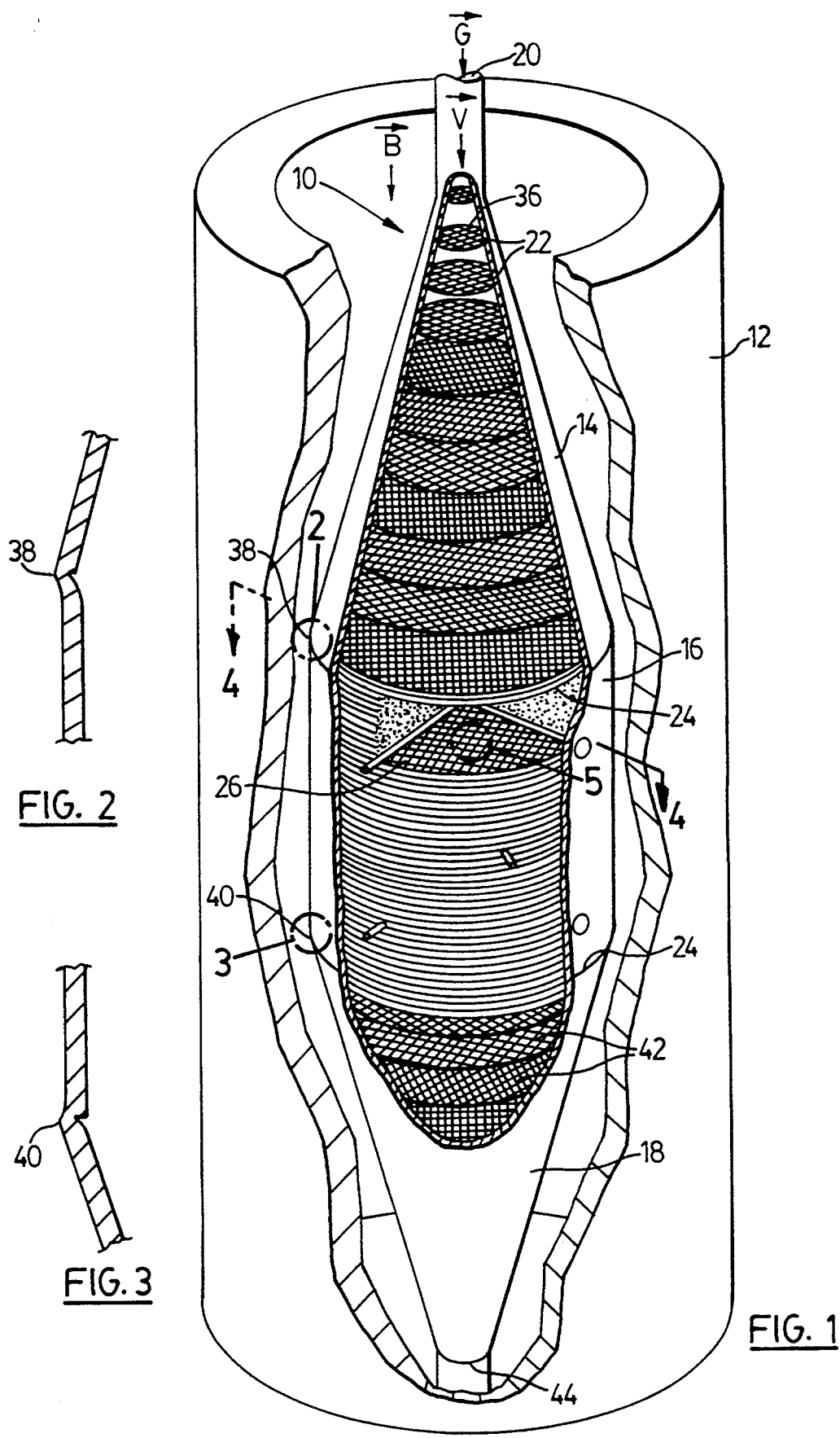
FIG. 1 is a perspective view of a preferred embodiment of a filter device made in accordance of the subject invention, shown within a solenoidal magnet, with the front partially broken away.
FIG. 2 is an enlarged detailed sectional view of area 2 in FIG. 1.
FIG. 3 is an enlarged detailed sectional view of area 3 in FIG. 1.

FIG. 1 illustrates a preferred embodiment of the filter device of the subject invention, shown generally as 10, mounted within a cylindrical magnet 12. Filter device 10 comprises inverted upstream conical funnel 14, a coaxial cylindrical filter chamber 16, and a coaxial downstream conical funnel 18.

Inverted conical funnel 14 expands and uniformly distributes the flow of fluid applied to the filter device 10, to give laminar flow and a uniform transverse velocity profile. The fluid enters device 10 at input opening 20 and flows downwardly in the direction of gravity G as shown by arrow V through upstream funnel 14. A plurality of longitudinally spaced upstream flow smoothing meshes 22 are mounted transversely across upstream funnel 14. Flow smoothing meshes 22 distribute the fluid uniformly outwardly as the cross-section of upstream funnel 14 expands. Meshes 22 preferably comprise woven, non-magnetisable wires 36 having a preferably circular cross-section. Wires 36 are preferably non-magnetic stainless steel wires having a diameter of 160 μm, and are spaced a minimum of 200 μm apart (38 gauge/70 mesh). Each smoothing mesh 22 is preferably rotated 45° relative to the previous mesh 22. Alternatively, thin plates with a multiplicity of uniformly distributed apertures therein could be used in place of meshes 22.

Upstream funnel 14 preferably has an inside surface which is highly polished to a smooth and continuous surface. In a preferred embodiment, inverted conical funnel 14 is made of Perspex TM plastic, has a height of 63 mm and a total included angle of 16.2°, large end diameter of 21 mm, and includes a minimum of 13 flow smoothing meshes 22, spaced longitudinally approximately 5 mm apart.

Cylindrical filter chamber 16 is coupled to upstream funnel 14 at intersection 38. Cylindrical filter chamber 16 comprises a cylindrical tube made of a plastic material, having mounted therein ordered wire array 24 comprising a multiplicity of closely packed magnetisable wire meshes 26. Ordered wire array 24 is a three dimensional array or matrix of wire meshes. Each magnetic mesh 26 preferably comprises a multiplicity of cross-hatched woven or knitted wires. Alternatively, mesh 26 could be made up of parallel wires supported by formers. Successive magnetisable meshes 26 are stacked on top of each other and axially rotated in such a manner that there are no straight paths for the fluid to travel through cylindrical filter chamber 16.

Downstream conical funnel 18 is coupled to cylindrical filter chamber 16 at intersection 40. Downstream funnel 18 narrows and collects the portion of the fluid which passes through chamber 16 while maintaining a smooth fluid flow. Downstream flow smoothing meshes 42 smooth the fluid flow as conical funnel 18 contracts the fluid flow from the larger cross-section of cylindrical filter chamber 16 to the smaller cross-section of output opening 44. Conical funnel 18 preferably has an inside surface which is highly polished to a smooth and continuous surface. The polished surface and its steep angle aid material coming into contact with the surface to continue to the outlet. Downstream conical funnel 18 is preferably made of the same material and has the same dimensions of upstream conical funnel 14.

Referring now to FIGS. 2 and 3, intersections 38 and 40 are slightly chamfered on the lower edge between the sections of the filter device 10 so as to maintain a smooth and continuous fluid flow between inverted conical funnel 14 and cylindrical filter chamber 16, and cylindrical filter chamber 16 and conical funnel 18 respectively. Chamfers in intersections 38 and 40 also eliminate any horizontal surfaces that the material may settle and accumulate on.

Conical funnels 14, 18, flow smoothing meshes 22, 42, and slightly chamfered intersections 38 and 40 are together adapted to avoid "diffuser stall", i.e. they produce laminar fluid flow and a uniform, flat transverse velocity profile between the container wall boundary layers. In the case of the conical funnels used in the preferred embodiment, it was found that the use of 13 smoothing meshes per funnel avoided diffuser stall.

Figure 5:
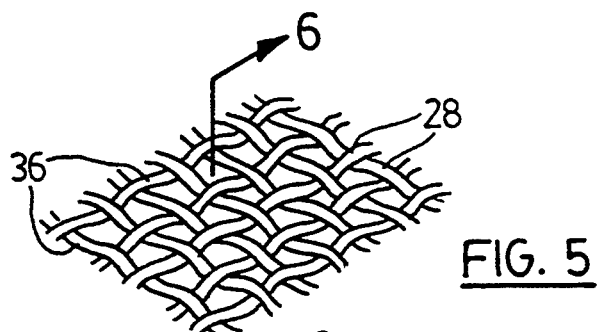
FIG. 5 is an enlarged detailed perspective view of area 5 in FIG. 1.

Referring now to FIGS. 1 and 5, filter meshes 26 comprise woven or knitted, magnetisable wires 27. Magnetisable wires 27 may comprise magnetisable stainless steel, preferably SS430, having a diameter between 22 μm and 150 μm, preferably with a diameter between 50 μm and 150 μm. Commercially available Knitmesh TM made of SS430 stainless steel wire was found to give good results.

Figure 4:
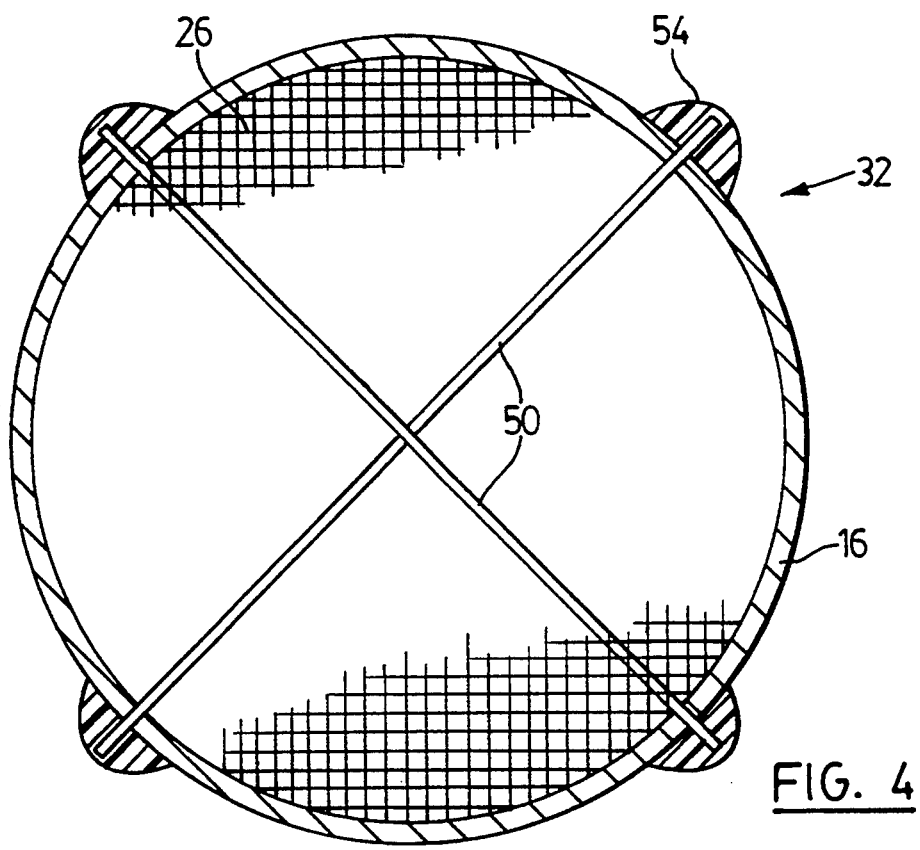
FIG. 4 is an enlarged transverse sectional view taken along lines 4—4 in FIG. 1, with the ordered wire arrays mostly broken away.

Referring to FIGS. 1 and 4, illustrated therein are mesh support means 32 for supporting meshes 26 against distortion due to fluid flow and applied magnetic field B. Mesh support means 32 comprises a plurality of longitudinally spaced pairs of intersecting support wires 50 extending transversely across cylindrical filter chamber 16. Pairs of support wires 50 are preferably spaced approximately 5 to 6 mm apart from each other. Support wires 50 protrude through the wall of cylindrical filter section 16, and are anchored in place with epoxy resin 54. Support wires 50 are preferably made of non-magnetisable stainless steel, have a diameter of 250 μm. The required spacing between pairs of support wires 50 is dependent upon the diameter of magnetisable wires in meshes 26, mesh construction, the strength of applied magnetic field B, and the flow velocity V.

Figure 6:
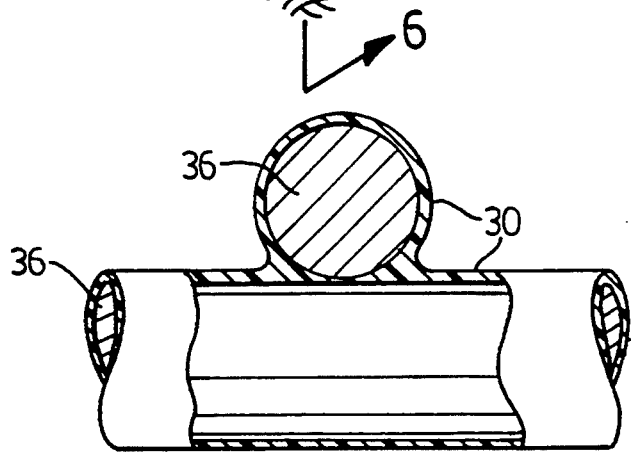
FIG. 6 is an enlarged detailed sectional view of a wire junction, taken along lines 6—6 in FIG. 5.

As shown in FIGS. 5 and 6, magnetisable wires 27 have silicone coating 30, with a thickness of a few percent of the diameter of magnetisable wires 27. Silicone coating 30 acts to crosslink magnetisable wires 27 at junctions 28, thereby preventing distortion of meshes 26 due to fluid flow and applied magnetic field B. Silicone coating 30 is preferably applied when magnetisable wires 27 have a diameter of less than 100 μm. In one embodiment, silicone coating 30 comprises Dow Corning 1107 fluid, and it is applied to magnetisable wires 27 by dipping them in a solution of 1% v/v solution in acetone. The acetone is then allowed to evaporate, and the silicone coating is heat cured at approximately 130° C.

As shown in FIG. 1, filter device 10 is positioned in the longitudinal configuration, i.e. the fluid flow V and the applied magnetic field B are in the same direction, and are perpendicular to the wire length of the ordered wire array. Applied magnetic field B is preferably uniform, with a preferred strength of 1 Tesla.

Alternatively, the ordered wire array could be reoriented so that the magnetisable wires are either exclusively along the length of the filter or both transversely and lengthwise through the filter. In these cases, it would be best if the magnetic field was directed transversely across the filter, i.e. 90° to the magnetic field direction shown in FIG. 1. Thus the applied magnetic field would be perpendicular to the magnetisable wire length.

In use, a sample containing magnetically labelled and unlabelled materials is directed into filter device 10 at input opening 20, and is expanded by inverted conical upstream funnel 14. Flow smoothing meshes 22 and chamfered intersection 38 provide uniform laminar fluid flow while preventing boundary layer separation. As the fluid enters cylindrical filter chamber 16, it travels through ordered array 24 of magnetisable wire meshes 26 in the presence of uniform strong magnetic field B produced by magnet 12. In the process, magnetised materials are retained on magnetised meshes 26. The fluid, including non-magnetic materials, passes through filter chamber 16 and into conical downstream funnel 18. As the fluid enters downstream funnel 18 its flow is contracted to the dimensions of output opening 44, and uniformly distributed by flow smoothing meshes 42. Use of the subject filter device provides relatively high recovery of preselected materials with relatively low retention of unwanted materials.

The filter device of the invention may be used to positively select materials, including viruses, bacteria, organelles, proteins, nucleic acids, organic molecules, mineral particles, and cells which express cell surface antigens recognized by antibodies, such as endothelial cells, hybridomas, erythrocytes, lymphocytes and tumor cells.

In a preferred embodiment of the invention, discussed in more detail below, cells or proteins are positively selected from biological fluids such as blood and bone marrow. Examples of such cells are cytotoxic T cells preferably those recognized by the monoclonal antibody OKT5; CD8+ cells from peripheral blood; CD34+ cells from bone marrow; tumor cells from bone marrow harvested for autologous transplantation.

Where the cells to be separated are from a biological fluid, enriched preparations of cells may be used as an initial sample. For example, where the cells are to be separated from bone marrow, an enriched sample of mononuclear cells may be used. An enriched sample of mononuclear cells may be obtained by preparing a buffy coat suspension and/or a carrying out density gradient separation using techniques known in the art (See Areman, E. M. et al., in Bone Marrow Purging and Processing, Vol. 333, Gross, S., Gee, A. P., and Worthington-White, D. A., Eds., Wiley-Liss, New York, 1990, 379; Gilmore, M. J. et al., Vox Sang., 45, 294, 1983; Faradji, A. et al., Vox Sang 55, 133, 1988; Gerota, J. et al, Cryobiology 19, 675, 1982; and Rowley S. D. et al., in Bone Marrow Purging and Processing, 333, Gross, S., Gee, A. P., and Worthington-White, D. A., Eds., Wiley-Liss, New York, 1990, 369; BeauJean, M. F. et al., Transfusion, 25, 152, 1985; English D., et al., Transfusion, 29, 12, 1989; Humblet, Y., et al., Bone Marrow Transplant, 3, 63, 1988; and Jin, N., et al., Exp. Hematol. 15, 93, 1987 which are each incorporated herein by reference). Where the cells to be separated are erythrocytes, the erythrocytes may be formalin fixed as described by Langlois et al., (Cytometry 11, 513, 1990) which is incorporated herein by reference. Enriched protein samples may be obtained using techniques known in the art such as precipitation, electrophoresis, affinity chromatography, gel filtration and immunoprecipitation.

The materials to be separated using the filter device of the invention may be magnetically labelled by conjugating the materials to magnetic or highly magnetisable particles, for example ferritin or ferrofluids. The term "ferrrofluids" refers to a concentrated colloidal solution containing particles consisting of a magnetic core, such as magnetite ($Fe_3O_4$,) coated with a surfactant which keeps the crystals from interacting. The core portion is generally smaller than 30 nm which is too small to hold a permanent magnetic field. The ferrofluids become magnets only when placed in a magnetic field. Examples of ferrofluids which may be used in the present invention and processes for preparing them are described by Kemshead J. T. in J. Hematotherapy, 1:35, 1992, at pages 36 to 39, which is incorporated herein by reference. Preferably, colloidal particles of Dextran-Iron complex (See Molday, R. S. and McEnzie, L. L. FEBS Lett. 170:232, 1984; Miltenyi et al., Cytometry 11:231, 1990; and Molday, R. S. and MacKenzie, D., J. Immunol. Methods 52:353, 1982) which are each incorporated herein by reference, are used in the method of the invention.

The materials may be conjugated to magnetic or highly magnetisable particles using techniques known in the art. For example, where the material is a cell or protein, antibodies specific to the cell or protein may be chemically bound to the surface of the magnetic or highly magnetisable particles using cyanogen bromide. When the complexes are reacted with a sample containing the protein or cells, conjugates will form between the proteins or cells and the magnetic or highly magnetisable particles.

Alternatively, the preselected cells or proteins may be conjugated to magnetic or highly magnetisable particles by means of antibody complexes. The antibody complexes may be bispecific antibodies or tetrameric antibody complexes. Bispecific antibodies may be prepared by forming hybrid hybridomas. The hybrid hybridomas may be prepared using the procedures known in the art such as those disclosed in Staerz & Bevan, (1986, PNAS (USA) 83: 1453) and Staerz & Bevan, (1986, Immunology Today, 7:241). In general, a hybrid hybridoma is formed by fusing a first cell line which produces a first monoclonal antibody which is capable of binding to at least one antigen on the surface of the magnetic or highly magnetisable particles and a second cell line which produces a second monoclonal antibody which is capable of binding to a preselected protein or at least one antigen on the surface of the preselected cells. The bispecific antibodies may also be constructed by chemical means using procedures such as those described by Staerz et al., (1985, Nature, 314:628) and Perez et al., (1985 Nature 316:354).

Bispecific chimeric monoclonal antibodies containing a variable region of an antibody for example, murine antibody, specific for at least one antigen on the surface of the magnetic or highly magnetisable particles, a variable region of an antibody which is capable of binding to a preselected protein or at least one antigen on the surface of the preselected cells and the constant regions of human immunoglobin such as human $IgG_1$, $IgG_2$, $IgG_3$ and $IgG_4$ antibody may also be constructed as described above.

A tetrameric immunological complex may be prepared by preparing a first monoclonal antibody which is capable of binding to at least one antigen on the surface of the magnetic or highly magnetisable particles and a second monoclonal antibody which is capable of binding to a preselected protein or at least one antigen on the surface of the preselected cells. The first and second antibody are from a first animal species. The first and second antibody are reacted with an about equimolar amount of antibodies of a second animal species which are directed against the Fc-fragments of the antibodies of the first animal species or the Fab fragments of such antibodies. The tetrameric complex formed is then isolated. (See U.S. Pat. No. 4,868,109 to Lansdorp, which is incorporated herein by reference for a description of methods for preparing tetrameric antibody complexes).

The sample containing the preselected protein or cells is reacted with the antibody complexes so that the preselected protein or cells present in the sample bind to the antibody complexes to form conjugates of the selected protein or cells and the antibody complexes. The reaction conditions are selected to provide the desired level of binding of the protein or cells and the antibody complexes. Where it is intended to separate a subpopulation of selected cells it is preferred that a sample of cells or enriched sample having a concentration of about $(1-5)\times 10^7$ cells/ml, is incubated with antibody complexes having a concentration in the range of about 0.001 to 10.0 µg/ml, preferably 0.01 to 1.0 µg/ml, for a period of about 30 minutes, at a temperature of about 4° C. A sample of cells containing complexes is then reacted with the magnetic or highly magnetisable particles to produce magnetically labelled cells or proteins in the sample. In one embodiment, a sample of cells containing complexes having a concentration of about $0.2-1.0\times 10^8$ cells/ml is reacted with a ferrofluid, preferably magnetic dextran-Fe particles (OD450 nm=0.01-0.1) for a period of about 30 minutes, at a temperature of about 4° C.

The sample containing the magnetically labelled materials is passed through a filter device of the invention in the presence of a magnetic field using the procedures outlined in detail above. In a preferred embodiment for separating preselected cells from a biological sample, a sample containing magnetically labelled cells and having a concentration of between about $4\times 10^6$ to $2\times 10^8$ cells/ml is passed at 0.5 ml/min through a filter of about 1.5 to 3 ml. The magnetically labelled conjugates are retained in the high gradient magnetic filter and the materials which are not magnetically labelled flow through the filter after washing with a buffer. A "purified" fraction containing the magnetically labelled cells is recovered by turning off the electromagnet. A "purified" cell fraction may be further analyzed using procedures such as flow cytometryanalysis. Dead cells may be identified using propidium iodide.

The following non-limiting example is illustrative of the present invention:

EXAMPLE

The following materials and methods were used in the investigations described in the example:

Antibodies

The mouse $IgG_1$ monoclonal OKT5 with specificity for CD8+ cytotoxic T cells (Bach, J. F. in Leucocyte Typing, eds. Bernard. A.. Boumsell. L.. Dausset. J., Milstein. C. & Schlossman. S. F.: Springer-Verlag. New York. 1984. pp 661–664, 1984) was purified from culture supernatants of the OKT5 hybridoma line obtained from ATCC CRL 8013 (American Tissue Culture Collection). The mouse $IgG_1$ anti-dextran monoclonal antibody (DX1) was purified from culture supernatants produced by a switch variant of the hybridoma 341G6 as described (Thomas et al. J. Immunol Methods). $F(ab')_2$ fragments of the rat monoclonal $IgG_1$ antibody TFL-P9 specific for the Fc portion of the mouse $IgG_1$ molecule were obtained by pepsin digestion of purified immunoglobulin as described previously (Thomas, T. E., et al., J. Immunol. Methods 120: 221, 1989). Tetramolecular antibody complexes were prepared by mixing the OKT5 antibody with the anti-dextran antibody (DX1) and then adding the $F(ab')_2$ rat anti-mouse $IgG_1$ antibody in a molar ratio of 1:4:5 respectively. A significant fraction (32%) of the resulting tetramolecular antibody complexes had dual specificity for cytotoxic T-cells and dextran.

Magnetic Particle Preparation

Submicron magnetic particles were prepared in a similar manner to that described by Molday and MacKenzie. (U.S. Pat. No. 4,452,773; J. Immunol. Methods 52: 353, 1982). Briefly, ten grams of Dextran T40 (Pharmacia. Uppsala. Sweden), 1.5 g $FeCl_3-6H_2O$ and 0.64 g $FeCl_2-4H_2O$ were dissolved in 20 ml $H_2O$ and heated to 40° C. The solution was continually stirred as 10 ml 4N NaOH was slowly added and the mixture heated to 70° C. for 5 min. The particle suspension was neutralized by adding acetic acid (glacial). Aggregates were removed by centrifuging at 1000 g for 5 min., then filtering through coarse Whatman filter paper followed by a 0.2 µm Millipore filter. Free excess dextran was removed from the magnetic particles by HGMS with a simple filter which consisted of a column (3 cc disposable syringe) packed (17%w/v) with fine (0.025 mm) stainless steel wire (AIS1302. Goodfellow Metals Ltd., Cambridge). Bubble formation around the stainless steel wire was prevented by initially filling the filter with 70%w/v ethanol followed by extensive washing with water and phosphate buffered saline (PBS). The suspension of dextran and iron was passed through the filter in a magnetic field of 1.0 Tesla generated by an electromagnet. Washed magnetic particles were eluted in PBS and the optical density (OD) at 450 nm was recorded. These dextraniron colloidal particles were stable in suspension at 4° C. for several months.

Filter Design and Construction Wire Array Construction

The layers of mesh making up the wire array were across the cross section of the filter chamber, parallel to the ends of the filter. The knitmesh wire array was constructed using a board with two upright pins in it, upon which successive layers of the mesh were impaled. Each layer of mesh was rotated 90° and flipped in relation to the previous layer. This was to ensure that no clear channels of fluid flow could occur through the wire array, i.e. no light could be seen through the array. After the requisite number of mesh layers had been placed on the pins, a filter chamber cross-section stencil was impaled on the pins. A pair of small sheet cutters was used to cut the mesh layers to form a cylindrical solid which became the wire array. It was desirable to minimize the wire array diameter to reduce the number of cells required in an experiment. A 21 mm diameter was the minimum that could be fabricated. The mesh layers were then secured together by a loop of 250 $\mu$m SS wire previously placed about the two impaling pins. The wire array was then siliconised and inserted in the filter chamber. For wire arrays of woven mesh: circular mesh pieces, stamped or cut out, were simply stacked while ensuring that there was no clear line of sight through the overall wire array. Wire arrays of various lengths were constructed, usually of longer length than that used in earlier work.

Wire Array Support

Wire arrays constructed of SS430 wire <100 $\mu$m diameter or not woven or knitted tend to experience some distortion from the fluid flow and the magnetic field with repeated use. To eliminate this problem the wires in the array were crosslinked to each other using a silicone coat. In addition, periodically through the wire array two 250 $\mu$m SS wires were placed across the cross-section of the filter chamber. The silicone coat was Dow Corning 1107 fluid (polymethyl hydrogen siloxane) as a 1% v/v solution in acetone. The wire array was dipped briefly in the solution, the acetone allowed to evaporate then the silicone heat cured (120°–150° C.) on the wires. The silicone coat thickness was only a few percent of the wire diameter. A brief comparison experiment between coated and un-coated wire arrays indicated that the silicone coat did not significantly affect; the magnetic separation process. All the filters here were siliconised. A single filter has been used for 43 individual separations without suffering any noticeable deterioration in its performance or appearance.

The Filter Container

Conical funnels above and below the wire array were required. The perspex conical funnel produced was 63 mm long with a total included angle of 16.2°. The inside surface was polished to a mirror finish and the complete piece annealed at 60° C. to relieve surface strain and prevent cracking and crazing at the edges. An identical piece was manufactured to serve as the downstream conical funnel. The leading edges of the wire array cylinder and the downstream conical funnel were slightly chamfered so that no horizontal surfaces were presented and to aid in the continuity of the boundary layer.

Since the funnel was over the threshold dimensions for diffuser stall, (Blevins R. D. "Applied Fluid Dynamics Handbook" Van Nostrand Reinhold Co. New York 1984), a series of longitudinally spaced meshes was incorporated to prevent stall. Finer mesh apertures produce better flow control, but a 200 $\mu$m limit was chosen to correspond to the smallest filter mesh aperture size in the Bone Marrow Collection Kit produced by the Fenwal Division, Baxter Healthcare Corp. Thus mechanical straining of cell clumps and aggregates should be minimal. The SS mesh was not appreciably magnetisable; plain weave; 160 $\mu$m wire diameter and 200 $\mu$m mesh aperture size (38 gauge/70 mesh). Thirteen flow meshes in each of the upstream and downstream conical funnels was chosen as the minimum to prevent boundary layer separation. The spacing of the meshes was approximately 5 mm. The flow velocity profile through the array was seen to be flat between the wall boundary layers. The wire array was coupled to the upstream and downstream conical funnels to form the complete filter. In use all the magnetised wires of the ordered wire array were perpendicular to the magnetic field and fluid flow, the "longitudinal configuration"; see Watson J. H. P., "High Gradient Magnetic Separation", Chapter 22 in: Solid-Liquid Separation, Third Edition, edited by Svarovsky L., Butterworths & Co. Publishers, 1990 and Parker M. R., "The Physics of Magnetic Separation", Contemp. Phys., 1977, Vol. 18, No. 3, p. 279–306, 1977.

Magnetic Separation Of Cells

Mononuclear cells were isolated from the peripheral blood of healthy, consenting donors using Ficoll Hypaque as described previously (Wognum, A W., et al., Cytometry 8: 366, 1987). In most cases the cells were cryopreserved and magnetic separations were conducted with thawed cells, Cells were resuspended at $2 \times 10^7$ cells/ml in Hanks' Buffered Saline with 2% Fetal Calf Serum and 0.1% Sodium Azide (HFN) and incubated with anti-dextran$\times$OKT5 tetrameric antibody complexes (0.5 $\mu$g OKT5/ml) on ice for 30 min. After one wash the cells were again resuspended at $2 \times 10^7$ cells/ml (HFN) and mixed with dextran-iron particles (final OD450=0.1), incubated on ice for 30 min. This "feed" suspension was then separated directly using HGMS. The "feed" suspension was passed through the filter at a range of flow rates using a peristaltic pump. The collected fraction was called the "flow through". The magnet was then turned off and a "purified" fraction collected at 14 ml/min. The following steps were followed to ensure good separation results:

1) Due to the size of the filters an excessive superconducting magnet with a warm bore was used to accommodate the filters in the longitudinal configuration at 1 T. Conventional, normal electromagnets could be manufactured to accommodate the filters, but for this work only the superconducting magnet was available.
2) The filters were always flushed with $\geq 3$ void volumes for the collection of each fraction.
3) For multiple successive separations the filter was always flushed through with distilled water between separations to lyse any remaining cells that may have carried over.
4) To accommodate the larger volumes of some fractions, 250 ml conical base centrifuge containers were used for collection. These containers were also advantageous for multiple separations where a rigid feed tube was placed at the apex of the base to ensure that all cells were returned for successive separation.
5) The maximum bulk flow velocity was used, $6.7 \times 10^{-4}$ m/s (14 ml/min), to minimize the separation time for these larger void volume filters, <90 ml. The long wire arrays would compensate for the reduced probability of capture per wire in order to still give high filter recoveries.

FACS Analysis (Fluorescent Activated Cell Sorting)

Feed, flow through and purified cell suspensions were stained with FITC conjugated F(ab')$_2$ fragments of sheep antimouse IgG (SAM-FITC, Cappell Cat-No. 1311.1744), $10^6$ cells were suspended in 100 μl of either SAM-FITC (diluted 1:100 with staining buffer) or DX1-FITC (1 μg/ml in staining buffer) incubated for 30 min on ice, then washed and resuspended. Stained and unstained samples were analyzed using a FACScan (Becton Dickinson, San Jose, Calif.) flow cytometer. % purities quoted herein are for viable cells only as determined by propidium iodide stain.

Investigations on positive and negative cell retention using the filter device of the invention were carried out as described below.

Zero Field Retention

In order for negative cells to be retained they need to be removed from the bulk fluid flow stream, with sedimentation the most likely mechanism. To study the sedimentation effect free of the variable cell adhesion properties of mononuclear cells, erythrocytes were used. The blood was obtained from the one donor, washed to obtain the erythrocytes, then stored in Alsever's media at 4° C. until used on the same day.

The cell concentration was the same as the feed used in the magnetic separations which was described above. This was to ensure that interparticle effects would be similar and to eliminate the formation of rouleaux. $2 \times 10^8$ erythrocytes in the usual media were used for the feed suspension.

For flow velocities of $(2.9-6.7) \times 10^{-4}$ m/s and flow through void volumes $\geq 3$ a retention of 0.20–0.35% was observed. The range was probably due to errors in handling small cell numbers in 10's ml of media. The retention attained was a factor of $\times 10$ improvement compared with an earlier filter where the erythrocytes were retained at a rate of 2.9% (range 2.2–3.3%, 3 expts). The wire array had no significant contribution. The retention of the tubing and pump system alone was of the order of 0.1% so the result obtained with the conical funnel filter probably represents the minimum practically attainable.

Five separations with peripheral blood mononuclear cells from four cryopreserved donors were conducted as described above at zero magnetic field to determine the negative cell retention. The cells were labelled as usual and $\geq 10^8$ total cells used for each separation. The flow velocities were $(2.9-.6.7) \times 10^4$ m/s and flow through was $\geq 3$ void volumes. The retentions for the positive and negative lymphocytes were not different but the monocytes were sometimes higher. The mean retention of 0.9%, n=10, range- 0.5–3.3% was obtained for monocytes and lymphocytes. This result was skewed by one high result for monocytes, 3.3%. Recalculating the mean equals 0.6±0.1%, n-9, range- 0.5–0.8%.The dead cells also gave a very low retention: mean=1.1±0.4%, n=5, range=0.7–1.8%. When the flow velocity was reduced to $1.4 \times 10^{-4}$ m/s the total retention increased to 1.6%.

The one high retention result obtained for monocytes, 3.3%, suggested that cells were still colliding with the filter surfaces but in the great majority of cases not adhering. The 3.3% result also indicates that there was probably a variable subpopulation of monocytes which are highly adherent to any surface, as is their nature. In addition the higher retention of previously cryopreserved mononuclear cells to the erythrocyte suggest that the former's increased retention was due to greater surface adhesion properties. An autologous cell prefilter could be used to remove highly adherent cell subsets, described as follows.

An autologous cell prefilter could be constructed to remove troublesome highly adhesive negative cells. A small fraction of the unlabelled feed could be pan leucocyte labelled, i.e. CD45, with dextran-iron and passed through the prefilter such that all the pan labelled cells were retained. The unlabelled feed could then passed through the prefilter to enable highly adhesive cells to be retained by the pan-labelled cells. To boost magnetically induced non-magnetic circulation interactions with the wire array, the unlabelled feed could be spiked with highly magnetically labelled erythrocytes. Alternatively the original pan labelled cells could be used in the same role as the erythrocytes, but separation conditions would have to ensure complete depletion of the pan labelled cells.

The wire array lengths used in the studies described above were up to $\times 12$ that used previously, and did not significantly contribute to the retention of any cell type at any length. To test whether siliconising the wire affected the retention of negative cells, a comparison experiment between filter 50 μm and an identical unsiliconised filter had been performed. Only $4 \times 10^7$ previously cryopreserved cells were used in order to minimize any interactions between negative cells and those positive cells magnetically retained on the wire array. The comparatively slow flow velocity of $1.4 \times 10^{-4}$ m/s was to reduce the fluid viscous drag on potentially adherent cells. There was no significant difference in performance between the two filters. Both filters retained 12% of the negative cells.

Positive Cell Recovery

The experimental and predicted recoveries obtained for the long wire arrays are given in Tables 1 and 2. It was apparent that some positive cells were still evading retention despite the virtually absolute 100% recoveries predicted. It was hypothesized that the very low expressors were non-magnetically labelled, as follows.

The synthesis of the dextran-iron particles initially produces a mixture of free excess dextran macromolecules and the dextran-iron particles. The mixture was magnetically separated using a random wire array filter. Such a crude magnetic separation, in conjunction with the magnetic induced nonmagnetic circulation effect, would ensure that some free excess dextran would contaminate the purified dextran-iron product. For the very low expressors, where the number of binding sites was relatively low, the macro-molecules of dextran would compete more efficiently for binding than the dextran-iron particles which may require multiple binding sites. Thus the very low expressors would experience increased nonmagnetic labelling but still present a FACS signature indicating that it was sufficiently magnetic for magnetic separation.

To reduce the level of free dextran contamination, the magnetic separation in the synthesis could be conducted with an ordered filter. In addition, a purification with gel filtration chromatography on Sephacryl S-300 as per Molday supra, 1982.

Purity and Non-magnetic Cell Retention

The purity of the positive (magnetic) cells in the retained fraction was dependent on the recovery of the positive cells and the negative (nonmagnetic) cells. The recovery of the positive cells was dominated by the magnetic and fluid viscous forces, and it was not dependent on the number of cells retained. Thus, the recovery of the positive cells was independent of the negative cell retention. The negative cell retention was explained as follows.

The retention of the negative cells at zero magnetic field was reduced to 0.9% using the conical funnel filter chamber and was not dependent on the wire array. The results of the negative cell individual recovery with successive separations for the long wire arrays in the CFF chambers are shown in Tables 3 and 4. The results for the dead cells were similar to the monocytes but sometimes twice as high. The retention of negative lymphocytes and monocytes for the first 1 T separation was considerably greater than the 0 T result. Clearly the increased retention of the negative cells was due to lodgement amongst the magnetically accumulated positive cells on the wire array. It was found that donor and cell type variations for the adhesion properties were dominating the variation in negative cell retention for the first separation.

For each of the second and third successive separations at 1 T the individual recoveries of all the negative cells were surprisingly uniform for a cell type given the variability for the first separation. The uniformity and increasing individual recovery with successive separations suggests that a subpopulation of more surface adhesive cells was being preferentially retained. In addition the mechanism for nonmagnetic collision with the wires was the same for all wire arrays. Although the later individual recoveries were high, their uniformity was encouraging in that countermeasures against negative cell retention could be reliably applied independent of the donor.

Despite the persistence of the negative cells to be retained, high purities were obtained for these separations. After the second separation at 1 T the purities were: 97.6% mean, 96.0–98.3% range for 5 previously cryopreserved donors over 5 experiments.

In the only two experiments where a third separation was performed the purity was for both >99%.

The negative cells with the high adhesion properties only represent a small fraction of the total cells at the second 1 T separation: 0.5% mean, 0.1–2.3% range for the same conditions as above; the monocytes contributing solely to the higher values.

For this work intercellular adhesion was the dominant problem. The use of something akin to the gel prefilters of Cell Pro or the novel autologous cell prefilter described above may be of benefit.

While what is shown and described herein constitutes various preferred embodiments of the device and method of the subject invention, it will be understood that various changes can be made to such embodiments without departing from the subject invention, the scope of which is defined in the appended claims.

TABLE 1

| Recoveries for the 50 μm Wire Array | | |
|---|---|---|
| Relative Number of Layers | Experimental % Recovery | Predicted % Recovery |
| Normal x1 | 73 ± 7% | 79% |
| (73 layers) | (4 donors over 6 separations) | |
| x3.1 | 78 ± 7% (2 donors over 4 separations) | 99.2% |
| x6.2 | 78 ± 3% (2 donors over 6 separations) | 100.0% |
| x12.5 | 94 ± 4% (1 donor over 3 separations) | 100.0% |

The "Normal" x1 results are for the wire array used in earlier filters.

The wire arrays vary only in number of layers (length).

The predicted recoveries for the particular wire array were those derived from the models of Watson (Watson J. H. P., "Theory of Capture of Particles in Magnetic High-Intensity Filters", IEEE Trans. Magn., Vol. MAG-11, No. 5, p. 1597–1599, 1975), Birss (Birss R. R., Gerber R. and Parker M. R., "Analysis of matrix systems in high intensity magnetic separation", Filtration & Separation, pp. 339–342, 1977) and Gerber (Gerber R. and Lawson P., "The HGMS Filter Performance Exponential Law", IEEE Trans Magn., Vol. 25, No. 5, 1989).

All the donors were previously cryopreserved peripheral blood mononuclear cells. A CD8 antibody was used.

In each experiment the initial feed suspension contained $(2-3) \times 10^8$ total cells.

TABLE 2

| Recoveries for the 150 μm Wire Array | | |
|---|---|---|
| Relative Number of Layers | Experimental % Recovery | Predicted % Recovery |
| Normal x1 (36 layers) | 75 ± 5% (5 donors over 7 separations) | 72% |
| x11.3 | 92 ± 3% (1 donor over 3 separations) | 100.0% |

TABLE 3

NEGATIVE LYMPHOCYTE Individual Recovery with Multiple Successive Separations

| EXPERIMENT | MAGNETIC FIELD (T) | | | |
|---|---|---|---|---|
| | 0 | 1 | 1 | 1 |
| I | — | 3.2% | 11% | 18% |
| II | — | 1.2% | 12% | 24% |
| III | 0.5% | 1.1% | 10% | — |
| | — | 4% | — | — |
| IV | 0.8% | 1.4% | 11% | — |
| | — | 2.0% | — | — |
| V | 0.7% | 1.5% | 13% | — |
| | — | 2.5% | — | — |

Experiment I was at a flow velocity of $2.9 \times 10^{-4}$ m/s, the others were at the usual $6.7 \times 10^{-4}$ m/s.

Experiment V was conducted with the long 150 μm wire array from Table 2. The others used the long 50 μm wire arrays of Table 1.

Different previously cryopreserved donors were used for each experiment.

In each experiment the initial feed suspension contained $(2-3) \times 10^8$ total cells.

TABLE 4

MONOCYTE Individual Recovery with Multiple Successive Separations

| EXPERIMENT | MAGNETIC FIELD (T) | | | |
|---|---|---|---|---|
| | 0 | 1 | 1 | 1 |
| I | — | 7.0% | 12% | 44% |
| II | — | 3.0% | 30% | 54% |
| III | 0.6% | 3.7% | 36% | — |
| | — | 8.0% | — | — |
| IV | 0.6% | 2.5% | 27% | — |
| | — | 3.5% | — | — |
| V | 3.3% | 7.3% | 32% | — |
| | — | 16% | — | — |

We claim:

1. A device for separating magnetic materials from non-magnetic materials in fluid using an applied magnetic field, the device having a longitudinal axis along which fluid flows and comprising:

a) upstream fluid flow expansion and distribution means for expanding and uniformly distributing the fluid flow from a smaller transverse cross-section to a larger transverse cross-section, comprising an inverted upstream funnel with a smaller input end and larger output end, and a plurality of non-magnetisable flow-smoothing surface means extending transversely of the longitudinal axis across the funnel and spaced apart from one another along the longitudinal axis;

b) filter means for magnetically filtering the magnetic materials from the fluid while allowing non-magnetic materials to pass through when a magnetic filed is applied thereto, comprising a filter input and a filter output and a coaxial filter chamber located on the longitudinal axis with the filter input coupled to the output end of the upstream funnel and the filter chamber having mounted therein an ordered array of magnetisable wires; and c) downstream flow contraction and distribution means for contracting and uniformly distributing the fluid flow from a larger transverse cross-section to a smaller transverse cross-section, comprising a downstream funnel having a larger input end coupled to the filter output and a smaller output end, and a plurality of non-magnetisable flow-smoothing surface means extending transversely of the longitudinal axis across the funnel and spaced apart from one another along the longitudinal axis.

2. The device as defined in claim 1, wherein the funnels are conical and the filter chamber is cylindrical.

3. The device as defined in claim 1, wherein the ordered wire array comprises a stack of magnetisable wire meshes extending transversely of the longitudinal axis.

4. The device defined in claim 3, wherein the wire meshes are made of woven stainless steel wire.

5. The device as defined in claim 3, wherein successive and adjacent meshes are axially rotated relatively to each other.

6. The device as defined in claim 3, wherein the filter means also comprises reinforcing means for reinforcing the ordered wire array against distortion due to fluid flow and applied magnetic field.

7. The device defined in claim 6, wherein the reinforcing means comprises crosslinking means for crosslinking the wires of the ordered wire array, comprising an encapsulating coating applied to the wires at their junctions.

8. The device defined in claim 7, wherein the encapsulating coating is silicone.

9. The device as defined in claim 7, wherein the reinforcing means also comprises mesh support means for supporting the magnetisable meshes of the ordered wire array, comprising a plurality of support wires spaced apart along said longitudinal axis and extending transversely of said longitudinal axis.

10. The device as defined in claim 9, wherein the mesh support means comprises pairs of crossed wires.

11. The device as defined in claim 1, wherein the ordered array extends along the longitudinal axis and comprises a stack of magnetisable wire meshes extending transversely of the longitudinal axis.

12. The device as defined in claim 1, wherein the flow-smoothing surface means comprise smoothing meshes of wire.

13. The device defined in claim 12, wherein the smoothing meshes comprise woven, non-magnetic stainless steel wires.

14. The device as defined in claim 13, wherein the non-magnetic wires are spaced apart by a minimum of 200 µm apart.

15. The device as defined in claim 1, wherein the inside surface of the conical funnels are smooth and continuous.

16. The device as defined in claim 1, wherein the flow distribution means also comprise chamfered intersections between the filter chamber and the funnels.

* * * * *